United States Patent [19]
Aemmer

[11] Patent Number: 5,178,008
[45] Date of Patent: Jan. 12, 1993

[54] METHOD AND APPARATUS FOR THE QUALITATIVE ASSESSMENT AND CLASSIFICATION OF YARNS DURING A YARN CLEARING PROCESS

[75] Inventor: Peter Aemmer, Wettswil, Switzerland

[73] Assignee: Zellweger Uster AG, Switzerland

[21] Appl. No.: 645,712

[22] Filed: Jan. 25, 1991

[30] Foreign Application Priority Data

Jan. 26, 1990 [CH] Switzerland .................. 259/90

[51] Int. Cl.⁵ .................................... G06F 15/46
[52] U.S. Cl. ............................ 73/160; 364/470; 364/552
[58] Field of Search ............... 73/160; 28/222, 223; 364/470, 550, 551, 552; 356/429, 430; 57/58.83

[56] References Cited

U.S. PATENT DOCUMENTS

| | | | |
|---|---|---|---|
| 3,263,499 | 8/1966 | Gith et al. | 73/160 |
| 3,303,698 | 2/1967 | Loepfe | 73/160 |
| 3,704,362 | 11/1972 | Kolby et al. | 364/552 |
| 3,729,635 | 4/1973 | Shottenfeld et al. | 364/470 X |
| 3,757,211 | 9/1973 | Goto | 73/160 X |
| 3,831,444 | 8/1974 | Sasaki et al. | 73/160 |
| 4,088,016 | 5/1974 | Watson et al. | 73/160 |
| 4,430,720 | 2/1984 | Aemmer | 364/552 |
| 4,758,968 | 7/1988 | Lord | 364/552 |
| 4,774,673 | 9/1988 | Aemmer | 364/552 |
| 4,891,974 | 1/1990 | Wassenhoven | 364/470 |

FOREIGN PATENT DOCUMENTS

236979  11/1985  Japan ........................... 28/222

OTHER PUBLICATIONS

Uster News Bulletin, No. 29, Nov. 1981; "The Uster System of Yarn Fault Control".

Primary Examiner—William A. Cuchlinski, Jr.
Assistant Examiner—G. Bradley Bennett
Attorney, Agent, or Firm—Burns, Doane, Swecker & Mathis

[57] ABSTRACT

For the purpose of establishing the clearing limit of a yarn clearing system, the yarn faults are determined, classified and counted. The parameters reference length and sensitivity are set in relation to the number of the corresponding clearer cuts on an orthogonal coordinate system. A clearing profile is thereby generated which represents the functional correlation between the quantity of all theoretically possible combinations of the yarn clearer setting parameters, and which reveals the number of clearer operations to be expected during clearing of the yarn for any combinations of the setting parameters.

14 Claims, 3 Drawing Sheets

5,178,008

METHOD AND APPARATUS FOR THE QUALITATIVE ASSESSMENT AND CLASSIFICATION OF YARNS DURING A YARN CLEARING PROCESS

BACKGROUND OF THE INVENTION

The present invention generally relates to the electronic clearing of yarn, in which the yarn passes through a measuring head that scans its cross-section and provides corresponding cross-section signals, and wherein deviations of these signals from given clearing limits are established so that those yarn faults can be cut out of the yarn when the signals exceed the clearing limits of one or more quality criteria. By the same token, the invention relates to the quality assessment of yarns by detecting yarn faults according to several criteria, and determining their respective numbers, for the purpose of establishing the clearing limits of a yarn clearing system, as well as the classification of uncleared and cleared yarns.

In one method of yarn clearing carried out in the USTER CLASSIMAT System, described in the Uster News Bulletin No. 29, August 1981, yarn faults are classified according to length and cross-section into a total of 23 classes for short thick places, double threads, long thick places and long thin places. With the aid of USTER KORRELATOR stencils, values for clearing parameters (i.e. reference length and sensitivity) are determined from the CLASSIMAT results taking users' requirements into consideration. The corresponding values for the fault cross-section, i.e. sensitivity, and for the reference length, which is the length over which the mean value of the yarn cross-section is formed, are set in a yarn clearing device. Thereafter, those faults which exceed the limits established by the chosen values are cut out of the yarn and replaced by a knot.

It is a fact that the cleared yarn still has yarn faults, to be precise those which were categorized as tolerable in the clearer setting. Thus, in respect of these non-cleared yarn faults, as well as the fact that a substantial number of yarn defects are actually caused by irregularities that are proper to the spinning process, there may be differences in quality between different bobbins of cleared yarn. However, such a difference in quality may also exist in relation to other parameters, such as, for example, the number of splices or knots, the number of neps, or the coefficient of variation of evenness (CV%). Additionally, there is also a difference in relation to the yarn fault classes used in the USTER CLASSIMAT.

The fact that two bobbins cleared by the same clearer and at the same setting generally may not have the same quality leads to the consideration that it is desirable for a yarn manufacturer to be able to differentiate between bobbins of cleared yarn according to quality criteria. This would indeed open up the interesting possibility of being able to provide branded products of different levels of quality, to thereby be able to sell the higher-quality products at better prices.

A qualitative differentiation of yarn bobbins cleared according to the same clearing parameters, on the basis of the results of an on-line classification into a plurality of yarn fault classes or on the basis of the CLASSIMAT classes or a similar scheme is, however, relatively complex and, additionally, not very meaningful in terms of textile technology. Indeed, since the coarse faults are cleared out in any case, only a few definitive CLASSIMAT classes remain. If, however, only a few classes are relevant, a disproportion results between the technical effort required for complete classification and its potential result. An additional factor is that, with only a few classes, the scope or range of possibilities is poor since the "quality pattern" related to the few classes is too rough.

It is therefore an objective of the invention to provide a novel method which permits a definitive and reproducible qualitative differentiation and classification of electronically cleared yarn, while using the least possible expenditure in terms of technology and cost.

It is another objective of the invention to provide a novel yarn clearing method and apparatus which is more efficient and more flexible and also less cumbersome to determine optimum clearing limits compared to the method traditionally used with the USTER CLASSIMAT system.

SUMMARY OF THE INVENTION

According to one aspect of the invention, the first-named objective is achieved by a method in which yarn cross-section signals are compared with classification limits in the form of clearing limits, which classification limits are more stringent in each case than the corresponding clearing limits. Each instance of exceeding a classification limit for the respective quality criterion results in a notation being made while leaving the relevant yarn section unaffected.

This approach constitutes a type of virtual yarn clearing which has two differences compared to the conventional, genuine yarn clearing. First, the threshold values of the virtual yarn clearing are more stringent than those of the genuine yarn clearing. Second, exceeding these threshold values designated as classification limits does not trigger a cut by the clearer, but only a registration, for example, an incrementing of a counter.

With the method according to this aspect of the invention, the yarn manufacturer is provided with the possibility of being able to make an assessment of the quality of the yarn manufactured with only very small additional expenditure in that the quality criteria are formed by the non-cleared "yarn faults". As is the case with the genuine yarn clearing, the virtual yarn clearing also takes place in a plurality of channels corresponding to various quality features such as long and short, thick and thin places so that both methods are fully compatible with each other. A further essential advantage for the yarn manufacturer consists in the fact that the latter is dealing with a field that is familiar to him from known yarn clearing. This means that the system of setting parameters and their correlation with yarn faults and their frequency are familiar to him, and therefore he does not have to learn any additional aspects and properties of the new method or have to adapt to it.

According to another aspect of the invention, the second stated objective is achieved by the fact that clearing threshold values for reference length and sensitivity can easily be brought into relation with the number of the corresponding clearer interventions to be expected if the yarn were actually being cleared with settings according to such values. To this end, a clearing profile is set up which represents the functional correlation between all theoretically possible combinations of available setting parameters and the corresponding quantity of clearer interventions. This profile reveals the number of clearer interventions to be expected for any desired combination of setting parameters.

If, for example, the reference length is plotted on the x-axis, the sensitivity on the y-axis and the number of clearer interventions on the z-axis of a three-dimensional, orthogonal system of coordinates, the clearing profile is formed by a surface bounded by the positive coordinate semiaxes and curved towards the origin. By determining the clearing profiles for given yarns in combination with given types of yarn clearers, it is possible to set up a forecast of the frequency of cuts to be expected for any desired combination of all the existing combinations of the setting parameters of a certain type of clearer. This is done by determining the point on the x-y coordinate plane corresponding to particular values for the clearing parameters and defining a vertical line on this point. The z coordinate of the point of penetration of this line through the clearing profile corresponds to the frequency of cuts to be expected at the given setting.

The invention further relates to a device for carrying out this method. The device has measuring heads for scanning the cross-section of a yarn to be assessed, a control device and evaluation units to which the measuring heads are connected. The control device contains a processor unit, in which yarn data signals supplied by the measuring heads and preprocessed by the evaluation units are collected, digitized and stored in memory areas, and the yarn data signals stored in the memory areas are processed. The previously described virtual clearing takes place during processing for a multiplicity of pairs of values of the setting parameters, during which virtual clearing the yarn signals are compared with a plurality of different classification limits. Each instance of exceeding a classification limit triggers a registration of a virtual clearer intervention.

BRIEF DESCRIPTION OF THE DRAWINGS

The foregoing features and advantages of the invention are described in greater detail below with reference to an exemplary embodiment and the drawings, in which.

DESCRIPTION OF THE ILLUSTRATED EMBODIMENTS

One type of method for the clearing of yarns and for the assessment of yarn faults is described in U.S. Pat. No. 4,430,720, the disclosure of which is incorporated herein by reference thereto. This patent discloses that a measuring head through which the yarn passes generates a voltage signal, the value of which is a measure of the cross-section or the diameter of the yarn that has just been scanned. This signal is continuously tested to determine whether it lies within a given tolerance range or exceeds the latter, and the length of each excess of this type is additionally established.

The disclosed device for carrying out the described method consists of a number of stages, each of which is assigned to a section of a bobbin machine comprising a number of bobbin places and which is fed at its input with the yarn scanning signal of a measuring head. Each stage has a main output, at which a signal appears that can be used for the control of a yarn separating device, auxiliary inputs for external commands and signals and auxiliary outputs for statistical data on the production of the corresponding bobbin place or control or warning functions derived therefrom. Additionally, all the stages have access to a central memory area where the diverse parameters necessary for signal analysis and for the triggering of control and warning functions, such as, in particular, the tolerance limits for transverse and longitudinal dimensions, are stored.

Figure 1:
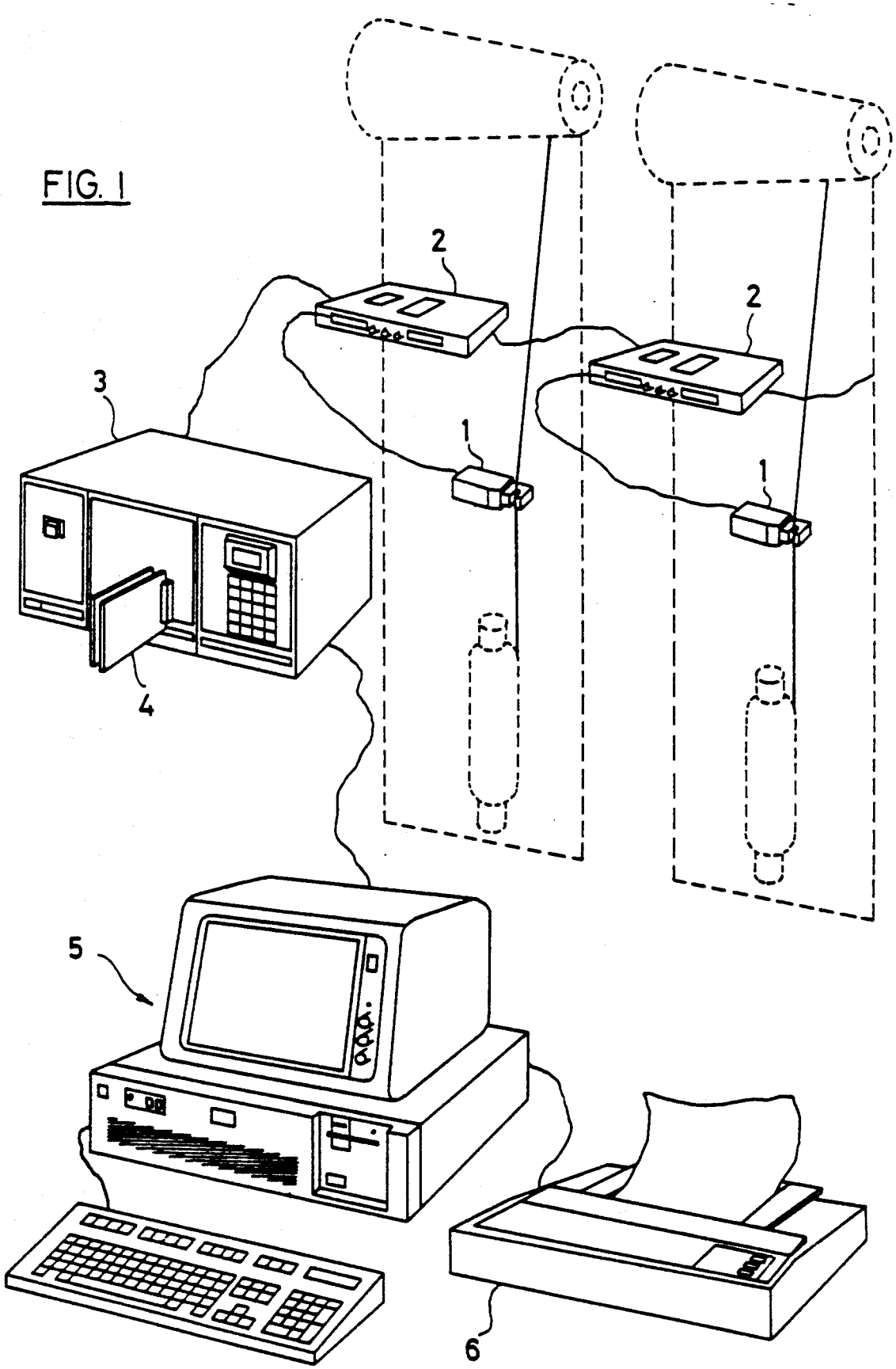
FIG. 1 is a block diagram view of a device for carrying out the method according to the invention.

FIG. 1 shows an overall illustration of a yarn fault classification system of this general type, but which operates in accordance with the present invention. As shown in the illustration, the system consists of a number of measuring heads 1 of the type also used for electronic yarn clearing, arranged on a winding machine. The measuring heads 1 are connected to evaluation units 2 which, in turn, are connected to a control device 3. This control device corresponds to that of the yarn clearing system USTER POLYGUARD with the so-called Q-package. The Q-package essentially comprises a processor unit 4 which undertakes the collection and buffering of the yarn signals originating from the measuring heads 1. This process includes receipt of the analog signals originating from the measuring heads 1, and storage of the digitized yarn signals in buffer store areas. This storage is done in such a way that yarn signals from the same measuring head are stored in a connected memory area, and these memory areas are organized and administered as "drum stores".

The processing unit 4 also processes the yarn signals stored in the memory areas. This includes processing one memory area after another in a structured period of time, and processing each memory area in such a way that a virtual clearing is carried out for a multiplicity of pairs of values for the reference length and the sensitivity.

More particularly, in accordance with one aspect of the present invention, each tolerance range or in any case certain tolerance ranges, the values of which form the so-called clearing limits, are assigned a second tolerance range with more stringent tolerance values. The values of the second tolerance range are stored in the central memory area. A cutting operation is triggered, if appropriate, when the yarn scanning signal falls outside a wider tolerance range with the clearing limits. When the tighter tolerance range is exceeded by the yarn scanning signal this condition only initiates a corresponding fault registration, without clearing the yarn.

The fault registrations are counted separately for the relevant quality features so that a total is obtained for each channel. The individual totals thus obtained are correspondingly weighted and an overall total is formed therefrom which then forms the criterion for the qualitative classification of the cleared yarn.

This method, designated hereinafter as "virtual" clearing, takes place, as in the case of the genuine yarn clearing, using the known channels or types of fault of short and long, thick and thin places, and it is, of course, at the discretion of the yarn manufacturer how he sets the limits. It has been shown that a virtual clearing which is set to be sensitive to short, thick and thin places may be of great interest to certain yarn manufacturers who supply yarn to manufacturers of prestige brands because fabric and knitted fabric having a comparatively large number of short, thick and thin places after dyeing have a far more unsettled product appearance.

In microprocessor-based yarn clearers, the virtual clearing is particularly easy to implement since the required additional expenditure is determined solely by the necessary algorithms. These algorithms are practically identical to those of standard yarn clearing, differing therefrom only by the particular limit values which are chosen. In addition, virtual clearing can readily be combined with standard clearing operations in terms of execution. As a result, the additional expenditure, measured in particular by the achievable result, is exceptionally small.

For a virtual clearing on the basis of short, thick and thin places, systems using measuring heads which apply the capacitive measuring principle are particularly well suited. In contrast, optical measuring systems are less well suited for this purpose, particularly if they involve a mere measurement of the diameter. Indeed in such a system, known and unavoidable forming effects in the yarn adversely appear as superimposed disturbances in the result of the measurement, in the case of short reference lengths.

Figure 2:
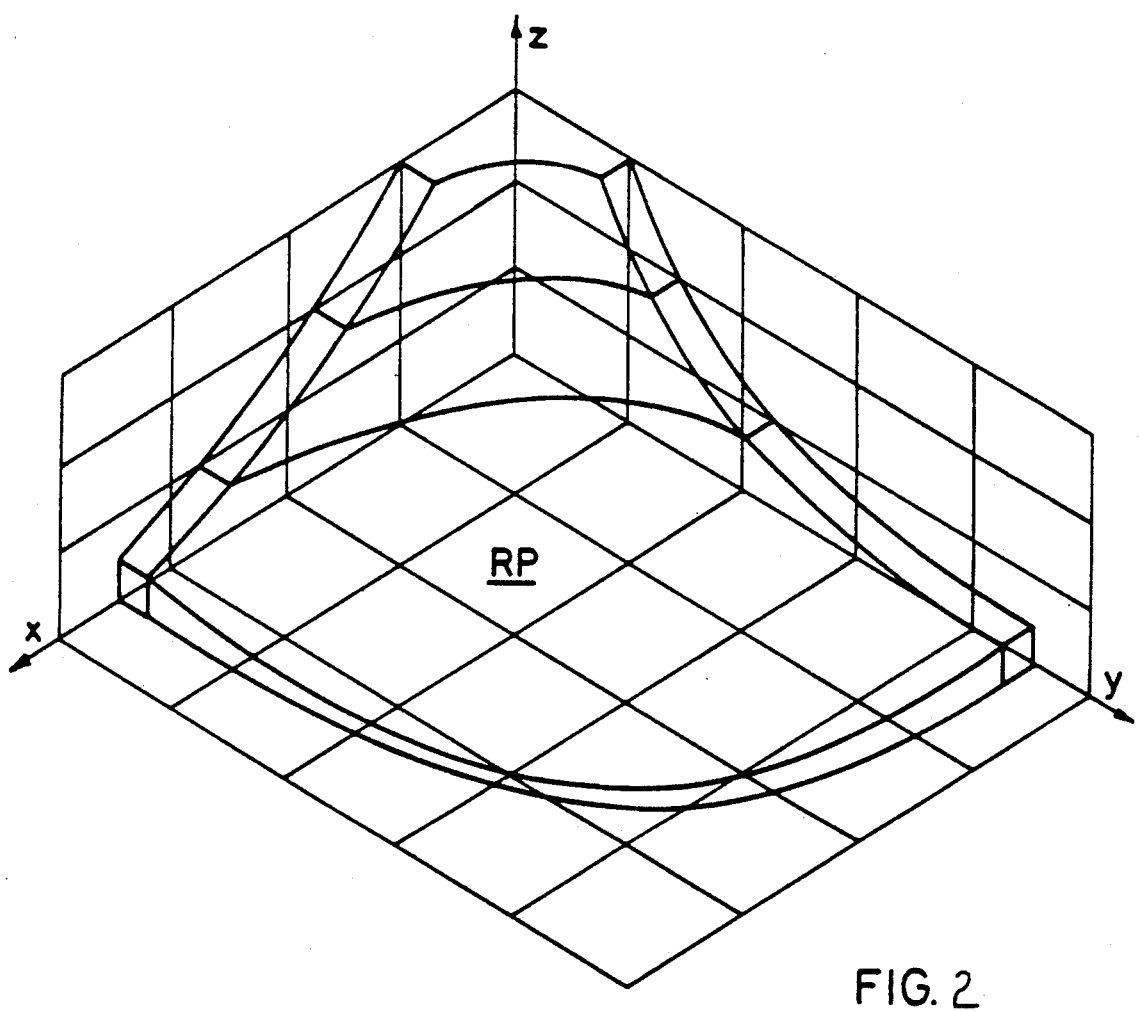
FIG. 2 is a perspective illustration of a clearing profile according to the invention.

Referring now to another aspect of the invention, FIG. 2 shows a three-dimensional, orthogonal system of coordinates, on the x-axis of which the so-called reference length (i.e. the length over which the mean value of the yarn cross-section is present) is plotted, on the y-axis of which the sensitivity (i.e. the fault cross-section) is plotted, and on the z-axis of which the frequency of cuts (the latter preferably in a logarithmic scale) is plotted for a particular yarn clearing system. The quantity of all the points with positive coordinates of the area bounded by these coordinate axes represents the quantity of all theoretically possible combinations of setting parameters and clearer cuts of all possible yarn clearing systems.

In a given yarn of a given length, the quantity of all theoretically possible combinations of the setting parameters (reference length, sensitivity) of a given yarn clearing system defines a quantity of clearer cuts to be expected for each of these possible combinations with the given yarn clearing system. Experience has shown that this quantity of clearer cuts is a constant and differentiable function of the quantity of possible combinations of the setting parameters, and it can be concluded therefrom that the number of clearer cuts resulting in every possible combination of setting parameters can be represented as a constant surface in the system of coordinates illustrated.

This surface, denoted in FIG. 2 as RP and hereinafter called the clearing profile, is the geometric position of the number of all clearer cuts in the clearing of a given yarn of a given length on a given yarn clearing system as a function of all desired combinations of the setting parameters of this yarn clearing system. Since, based on experience, the number of clearer cuts to be expected generally increases for every yarn existing in practice with a decreasing reference length and decreasing sensitivity of a yarn clearer, the clearing profile has the form shown in FIG. 2, which is curved inwards or concavely relative to the origin of the coordinates.

The determination of the clearing profiles of special types of clearing for given yarns of a given length takes place by the fact that individual sample values are determined by measurement and, from these, the intermediate values required for the representation of the profile are calculated algorithmically by interpolation and smoothing taking the statistical uncertainty into account. Establishing the sample values of the clearing profile by measurement takes place by the fact that a yarn clearer is constructed in such a way that it carries out a virtual clearing of the type described above, with reference to the more stringent set of limit values. Thus, this means that the yarn clearer will register and count the instances in which the yarn parameters exceed the respective threshold values for all channels and for all possible classification limits.

When these clearing profiles have been determined, it is possible to set up a forecast of the frequency of cuts to be expected for any desired combination of all the existing combinations of the setting parameters of a type of clearer by determining the point on the x-y coordinate plane corresponding to a certain setting of the clearing parameters and raising a vertical line at this point. The z coordinate of the point of penetration of this vertical line through the surface of the clearing profile then corresponds to the frequency of cuts to be expected at the given setting.

Referring again to the system shown in FIG. 1, the processing unit 4 selects the pairs of values which are decisive for virtual clearing in such a way that they reside inside an area of interest for the application of an orthogonal system of coordinates defined by the reference length and sensitivity axes in such a way that the density of these pair of values is high near the origin of the system of coordinates and decreases with increasing distance.

The processing unit preferably selects a system of coordinates in which one or both axes is/are calibrated according to a linear, a logarithmic or an approximately logarithmic scale. When a yarn sample is scanned, the processing unit stores the results of the virtual clearing in buffer areas in such a way that the results of yarn signals from the same measuring head are stored in each case in a connected buffer area, and these buffer areas are organized and administered as "drum stores".

As is further evident from FIG. 1, the control device 3 is connected to a personal computer 5, to which a printer 6 is also connected. The use of the personal computer 5 has, inter alia, the advantage that its screen is available to illustrate the results. For this illustration, the following possibilities are provided:

Three-dimensional graphic illustration of the clearing profile which can be supplemented on the screen, if required, by the functions "zoom" and "rotation".

Two-dimensional illustration of the clearing profile as a coded standard projection, to be precise either in a rectangular tabular form similar to the illustration in the USTER CLASSIMAT, the support values being plotted in the individual squares, or in the form of "height curves" of equal frequency of cuts.

In the types of illustration mentioned, a cursor is preferably superimposed on the screen, which cursor can be moved by means of a suitable input medium on the plane of the x-y axes. The value of the frequency of cuts corresponding to the coordinates (setting values) of the cursor is then illustrated in the three-dimensionally illustrated clearing profile as a point of penetration and/or in a bar of text as a numerical value.

This forecast value of the frequency of cuts directly displays the number of clearer cuts to be expected at the relevant clearer setting and thus makes the handling of stencils and the like superfluous.

Figure 3:
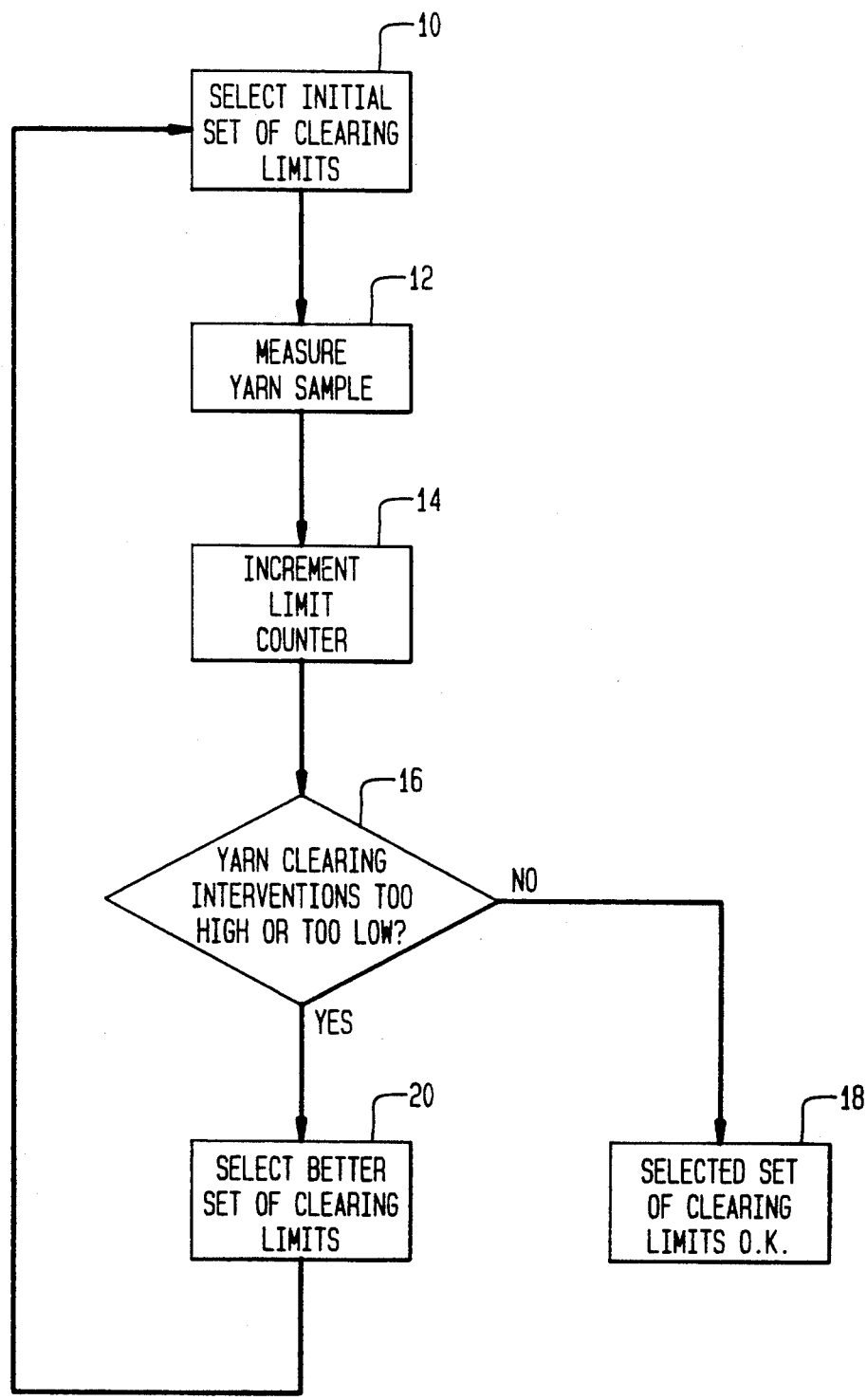
FIG. 3 is a flow chart of the operation of the device illustrated in FIG. 1.

To further facilitate an understanding of the various features of the invention, an example of the operation of the invention will be explained, with reference to the flowchart illustrated in FIG. 3 of the application. This flowchart depicts various steps carried out within the control device 3 during a yarn clearing and classification operation according to the present invention.

At the outset of the operation, an initial set of clearing limits is established (step 10). Thereafter, samples of the yarn to be processed are passed through measuring heads 1 (step 12). For example, each sample may comprise a suitable length of yarn from each bobbin whose yarn is to undergo a clearing operation.

As the samples of the yarn pass through the measuring heads, they are checked to determine the number of the yarn clearing interventions resulting at the selected initial set of clearing limits. Each time the yarn dimensions fall outside of the clearing limits, this fact is recorded and stored in an area of the processing unit's memory which is associated with the bobbin from which the yarn sample was taken. For example, each time that the parameters of the yarn fall outside of the range of the clearing limits, a corresponding count value stored in the associated area of the memory is incremented (step 14).

Once the length of the sample has been processed in this manner, the count value is analyzed whether the yarn clearing interventions corresponding to this value would be too high or too low (step 16). If they are not, the selected initial set of clearing limits is o.k. (step 18), if they are too high or too low, a better set of clearing limits is selected (step 20).

For determining a clearing profile of the type illustrated in FIG. 2, a multiplicity of sets of clearing limits, i.e. the virtual clearing limits, are established and a sample of yarn is tested to determine the corresponding numbers of yarn clearing interventions. Each set of clearing limits has a corresponding count value stored in an associated area of the corresponding unit's memory.

Once the length of the sample has been processed in this manner, a clearing profile of the type illustrated in FIG. 2 is determined for the yarn on the bobbin from which the sample is taken. More particularly, each set of virtual clearing limits defines a point on the x-y plane of the orthogonal coordinate system. For example, a virtual clearing limit can be defined in terms of a specific reference length (x-axis value) and a particular sensitivity (y-axis value). The corresponding count stored in the memory of the processing unit 4 determines the z-axis value at this point on the x-y plane. After all of these count values are plotted in the orthogonal coordinate system, adjacent sets of values are used to interpolate the z-axis values for points intermediate the actual measured values, and thereby define the concave profile illustrated in FIG. 2.

The clearing profile can then be employed in the selection of an appropriate yarn for a given customer and the setting of the proper limits for a clearing operation. For example, a customer may require yarn having a sensitivity of at least 70%. Using the clearing profile, an operator can determine which set of clearing limits provides an optimum result within this requirement, i.e. results in the fewest number of clearing cuts to the yarn during the clearing operation. Once this optimum set of clearing limit values is determined, the clearing apparatus can be appropriately set and the yarn passed therethrough to carry out the clearing operation.

Furthermore, if the operator determines that the theoretically optimum set of clearing limits for a given yarn would still result in an unacceptable number of knots in the yarn, this information will enable him to reject the yarn from that particular bobbin as being unsuitable for the desired purpose, and enable him to select a different bobbin which may meet the customer's needs more satisfactorily.

Thereafter, the results of the virtual clearing operation can be used to differentiate various cleared yarns according to quality criteria. This ability to differentiate between the yarns offers value-enhancing market advantages. For example, each bobbin can be appropriately marked or otherwise identified to indicate the results of the virtual clearing operation. For example, the bobbins can be provided with a label which indicates the number of faults of each class which were detected in the yarn during the virtual clearing operation but which were not actually cleared out of the yarn. As an alternative, the total count for each class of fault can be weighted and all of the weighted counts summed to provided a qualitative classification of the yarn.

Instead of providing a label on the bobbin to indicate classification, a sorter can be associated with the bobbin machine which directs the bobbins onto different tracks which respectively correspond to the different qualities of yarn. With this approach, the bobbins are automatically sorted according to quality.

In the foregoing example, a separate clearing profile is determined for the yarn from each defined bobbin. This approach is preferable because the yarn on each bobbin may be the product of different respective spinning lines, each of which has its own characteristic faults. However, it may be the case that all of the yarns produced from a certain spinning line regularly exhibit the same type and number of faults. In such a situation, it may be possible to use a single clearing profile for all bobbins of yarn produced from that spinning line, rather than generating a separate clearing profile for each bobbin.

Even though an orthogonal Cartesian system of coordinates has been illustrated in FIG. 2, this illustration is by no means to be understood as restrictive, and other systems of coordinates can, of course, also be used.

Also, the terms reference length and sensitivity which have been used in connection with the clearing limits are not to be understood as meaning that other parameters could not be used for setting up the clearing profile. For example, instead of the reference length, the fault length and, instead of the sensitivity, the change in cross-section can be used. In addition, or as an alternative to determining yarn faults, the quality assessment of the yarn can also take place by determining the imperfections, which are understood to be the so-called "frequent" faults, that is to say thin places, thick places and neps which are not classified as traditional faults and which are also generally not cleared out. In respect of these imperfections, reference is made to the publication USTER News Bulletin, No. 26, Nov. 1978, chapter: "The confidence limits of thin places, thick places and neps".

What is claimed is:

1. A method for establishing the clearing limits for a certain type of yarn to be cleared in production, comprising the steps of experimentally testing a sample of the same type of yarn to determine for a multiplicity of sets of clearing limits the corresponding numbers of yarn clearing interventions, generating by interpolation a clearing profile for the yarn which represents the relation between all possible combinations of the clearing limits and the corresponding number of yarn clearing interventions, and using said clearing profile to select the optimum compromise between yarn quality and the number of clearer interventions for the yarn to be cleared in production.

2. A method according to claim 1, wherein said yarn parameters include reference length and sensitivity, which are each plotted on one axis of a three-dimensional system of coordinates, and the number of clearing operations is plotted on a third axis of said system of coordinates so that the clearing profile is formed by a surface bounded by the positive coordinate semiaxes.

3. A method according to claim 2, wherein the determination of the multiplicity of sets of clearing limits includes the steps of simultaneously virtual clearing all sample values of a given pair of setting parameters, comparing yarn test signals with a plurality of classification limits corresponding to respective support values, and recording each instance in which a classification limit is exceeded.

4. A method according to claim 3, wherein the clearing profile is illustrated in the form of a three-dimensional graph.

5. A method according to claim 3, wherein the clearing profile is illustrated two-dimensionally as a coded standard projection.

6. A method according to claim 5, wherein the clearing profile is illustrated as a table containing a plurality of squares, in the individual squares of which table the sample values appear.

7. A method according to claim 5, wherein the clearing profile is illustrated in the form of curves with equal frequency of cuts in each case.

8. A method according to one of claim 1 wherein at least one of fault length and change in cross-section are used as parameters for setting up the clearing profile.

9. A method according to claim 1 wherein imperfections which are frequent faults generally not cleared, are used for the quality determination of the yarn.

10. A device for qualitatively assessing yarns, comprising:

measuring heads for scanning the cross-section of yarns to be assessed;

evaluation units for receiving and preprocessing signals from the measuring heads; and a control device including a memory in which preprocessed yarn signals from the evaluation units are collected, and a processor unit for processing the stored yarn signals relative to a multiplicity of pairs of values of setting parameters by comparing the yarn signals with a plurality of different classification limits that form sample values and recording each instance in which a classification limit is exceeded to indicate a yarn clearing operation, and for generating a clearing profile that correlates frequency of yarn clearing operations relative to said different classification limits, said processing unit illustrating said clearing profile in the form of a three-dimensional graph on a screen connected to the control device.

11. A device according to claim 10, wherein the pairs of values of the setting parameters lie within an area of interest for the application of an orthogonal system of coordinates defined by axes representing reference length and sensitivity in such a way that the density of the sample values is high near the origin of the system of coordinates and decreases with increasing distance therefrom.

12. A device according to claim 11, wherein the number of recorded instances is plotted on the third axis of the system of coordinates.

13. A device according to claim 12, wherein said control device causes a cursor to be superimposed on the screen, which can be moved on the plane of the x-y axes of the system of coordinates, and said control device further displays a value, corresponding to the coordinates of the cursor, of the number of clearing cuts to be expected as a point of penetration of a vertical line raised on the intersection of these coordinates through the clearing profile.

14. A device according to claim 13, wherein the display of the values for the respective point of penetration takes place in a tabular field.

* * * * *